United States Patent [19]

Harita et al.

[11] 3,940,422

[45] Feb. 24, 1976

[54] AROMATIC CARBOXYLIC AMIDE DERIVATIVES

[75] Inventors: Kozaburo Harita, Hongo; Yukiyoshi Ajisawa, Okaya; Kinji Iizuka; Yukihiko Kinoshita, both of Matsumoto; Tetsuhide Kamijo, Shiojiri; Michihiro Kobayashi, Toyoshina, all of Japan

[73] Assignee: Kissei Yakuhin Kogyo Kabushiki Kaisha, Japan

[22] Filed: Jan. 17, 1974

[21] Appl. No.: 434,252

[30] Foreign Application Priority Data
Jan. 18, 1973 Japan.................................. 48-7359

[52] U.S. Cl...... 260/340.5; 260/501.11; 260/518 R; 260/518 A; 260/519; 424/282; 424/319

[51] Int. Cl.²................................ C07D 317/50
[58] Field of Search............ 260/518 A, 518 R, 519, 260/501.11, 340.5

[56] References Cited
UNITED STATES PATENTS
3,488,737   1/1970   Gordon........................... 260/518 R

*Primary Examiner*—Anton H. Sutto
*Assistant Examiner*—L. A. Thaxton
*Attorney, Agent, or Firm*—William J. Daniel

[57] ABSTRACT

Novel aromatic carboxylic amides of the general formula:

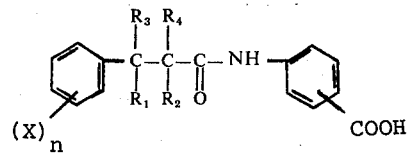

wherein each of $R_1$ and $R_2$ is a hydrogen atom or an alkyl group having 1–4 carbon atoms, $R_3$ and $R_4$ are hydrogen atoms or together form another chemical bond, each X is a hydroxyl group, a halogen atom, an alkyl group having 1–4 carbon atoms and an alkoxy group containing 1–4 carbon atoms, and n is an integer of 1–3, with the proviso that when two Xs are alkyl or alkoxy groups, they may be connected together to form a ring, as well as pharmaceutically acceptable salts thereof.

These compounds possess a strong antiallergenic action and are thus useful for treatment of asthma, hay fever, anticaria and atopic dermatitis.

The above aromatic carboxylic amides can be prepared by reacting a reactive functional derivative of the general formula:

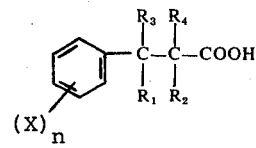

wherein $R_1$, $R_2$, $R_3$, $R_4$, X and $n$ have the same meanings given above, with an aminobenzoic acid of the formula:

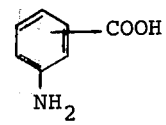

and, if desired, converting the resulting amide into the corresponding salts.

7 Claims, 7 Drawing Figures

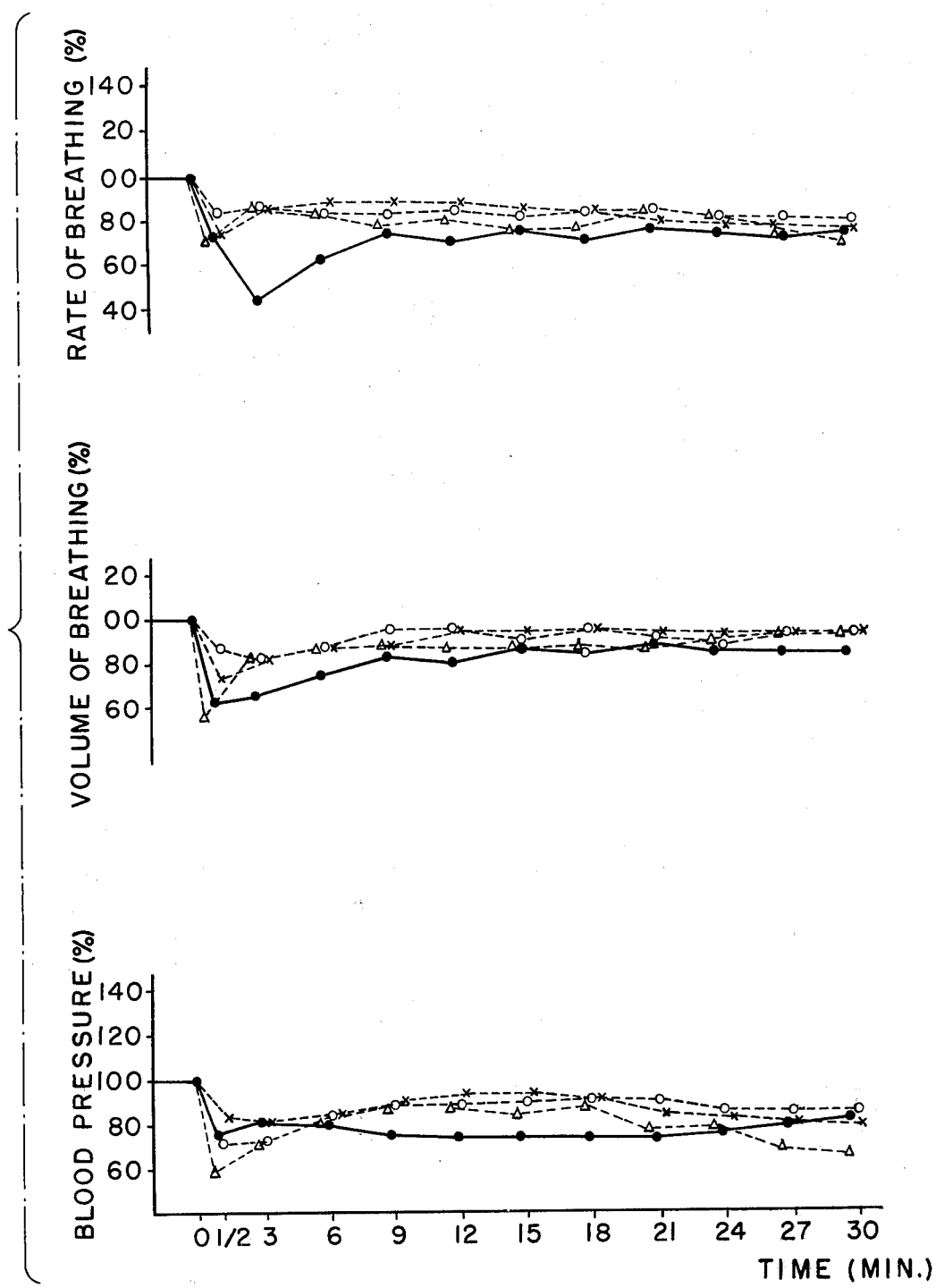

AROMATIC CARBOXYLIC AMIDE DERIVATIVES

BACKGROUND OF THE INVENTION

This invention relates to novel aromatic carboxylic amide derivatives. More particularly, this invention relates to nucleus-substituted cinnamoylaminobenzoic acid derivatives and nucleus-substituted hydrocinnamoylaminobenzoic acid derivatives exhibiting a strong antiallergenic action when administered orally to mammalia including humans.

Up to now, disodium cromoglycate was only one drug that inhibits the disruption of mast cells and release therefrom of chemical mediators. However, this compound loses its pharmacological effect when administered orally, and the extent to which this compound is applicable is naturally limited. Thus, development of an antiallergic agent which can display a sufficient therapeutic effect by oral administration has long been demanded in the field of medicine.

On the other hand, nuclei-unsubstituted cinnamoylaminobenzoic acid was already synthetized by Reinicke and publicly known (Liebig's Annalen der Chemie, Vol. 341, pages 94–96). However, this compound shows only a slightly weak antiallergenic effect when administered orally to mammalia, and so was hardly useful as a practical medicament.

BRIEF SUMMARY OF THE INVENTION

Accordingly, it is an object of this invention to provide a compound which exhibits a strong antiallergenic action when administered orally to mammalia including humans.

It is another object of this invention to provide a new aromatic carboxylic amide derivative possessing a pharmacological effect.

It is still another object of this invention to provide a nucleus-substituted cinnamoylaminobenzoic acid and a nucleus-substituted hydrocinnamoylaminobenzoic acid and the physiologically acceptable salts thereof.

Other objects, features and advantages of this invention will become apparent as the description proceeds.

The attached single drawing is a graph showing the change in physiological state with the lapse of time when the compound of this invention is administered to rats experimentally catching asthma.

DETAILED DESCRIPTION OF THE INVENTION

It has now been found that a compound of the general formula:

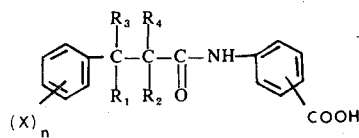

(I)

wherein each of $R_1$ and $R_2$ is a hydrogen atom or an alkyl group having 1–4 carbon atoms, $R_3$ and $R_4$ are each a hydrogen atom or together form another chemical bond, each X is a hydroxyl group, a halogen atom, an alkyl group having 1–4 carbon atoms and an alkoxy group having 1–4 carbon atoms and may be the same or different, and $n$ is an integer of 1–3 with the proviso that when two Xs are alkyl or alkoxy groups, they may be connected together to form a ring, can inhibit an experimental anaphylaxis (for example, inflammation of skin caused by an antigen-antibody reaction between reagin and its peculiar antigen) when administered orally to patients. It has also been found that this compound inhibits disruption of mast cells caused by a certain kind of an antigen-antibody reaction (for example, an antigen-antibody reaction between a reaginic antibody and its peculiar antigen) and the subsequent release of chemical mediators from the mast cells.

In view of these characteristic properties, it is expected that this compound possesses an antiallergenic action and is effective for the therapeutical treatment of diseases caused by allergies, such as asthma, hay fever, articaria and atopic dermatitis. In fact, this compound was found to be effective to alleviate symptoms in respiration and blood pressure observed in experimental asthma of mammalia.

The compounds of this invention are characterized by the presence as a nuclear substituent of at least one substituent selected from hydroxy, alkyl and alkoxy groups and halogen atoms. If the compounds are free of any such substituent, they become weak in antiallergenic action and less valuable for practical use. In case the nuclear substituent is one or more alkyl or alkoxy groups, they may be linear or branched. Within the range of 1-4 carbon atoms in such groups, no significant change was found in pharmacological effect. Where the nuclear substituents are two alkyl or alkoxy groups, they may be connected together to form a cyclic group. For example, methylenedioxycinnamoylaminobenzoic acid also possesses a strong antiallergenic action. The halogen atoms as nuclear substituents may be chlorine atoms, fluorine atoms and bromine atoms. The compounds having such nuclear halogen atoms are similarly strong in antiallergic action. The number of the nuclear substituents is limited to 1–3. In general, however, pharmacological activity becomes higher as the number of nuclear substituents increases. Compounds carrying as nuclear substituent a hydrophilic group such as a 2,3-dihydroxypropoxy group or a carboxymethoxy group are extremely weak in pharmacological activity.

In the compounds of this invention, the carboxyl group in the aminobenzoic acid residue may be in any of the 2-, 3- and 4-positions. Salts of compounds having this carboxyl group, such as alkali metal salts, are as high in the pharmacological effect as the corresponding compounds having free acid groups, while the compounds in the form of esters with a lower alcohol were found to be inferior in pharmacological activity.

Compounds of the general formula (I) can be prepared, for example, by a process wherein a reactive functional derivative of an aromatic carboxylic acid of the general formula:

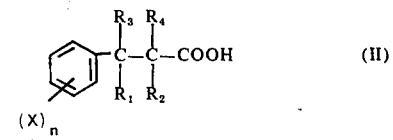

(II)

wherein $R_1$, $R_2$, $R_3$, $R_4$, X and n have the same meanings as given above, is reacted with an aminobenzoic acid of the formula:

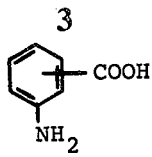

(III)

Alternatively, an aromatic carboxylic acid or a reactive functional derivative thereof of the above general formula (II) can be reacted with an aminobenzoic ester of the general formula:

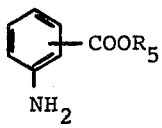

(IV)

wherein $R_5$ is an alkyl group having 1–4 carbon atoms, to provide an aromatic carboxylic amide derivative of the general formula:

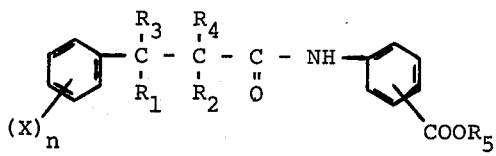

(V)

wherein $R_1$, $R_2$, $R_3$, $R_4$, $R_5$, X and $n$ have the same meanings as given above, and then this derivative is hydrolyzed to convert the ester group into a free carboxylic group.

Furthermore, the compounds of the general formula (I) can be prepared by halogenating a hemiester of malonic acid, reacting the halogenated product in an inert organic solvent such as chloroform with an aminobenzoic acid of the general formula (III) or an ester of the general formula (IV) in the presence of a base, such as a tertiary amine, hydrolyzing the resulting product to form an amidocarboxylic acid and condensing the amidocarboxylic acid according to the Knoevenagel reaction with a nucleus-substituted benzaldehyde corresponding to a carboxylic acid of the general formula (II).

The aromatic carboxylic acids of the above general formula (II) are known compounds and can easily be prepared according to methods disclosed in literature. Aromatic carboxylic acids having an unsaturated bond involve the two isomers, i.e., cis-form and transform, and either may be employed for the process of this invention. Examples of the aromatic carboxylic acids of the general formula (II) include aromatic unsaturated carboxylic acids, such as 2-, 3- or 4-methylhydrocinnamic acid, 2-, 3- or 4-ethylhydrocinnamic acid, 2-, 3- or 4-propylhydrocinnamic acid, 2-, 3or 4-hydroxyhydrocinnamic acid, 2-, 3- or 4-methoxyhydrocinnamic acid, 2-, 3- or 4-ethoxyhydrocinnamic acid, 2-, 3- or 4-chlorohydrocinnamic acid, 2-, 3- or 4-bromohydrocinnamic acid, 2-, 3- or 4-fluorohydrocinnamic acid, 2,3-dimethylhydrocinnamic acid, 3,4-methylenedioxyhydrocinnamic acid, α-methyl-4-ethylhydrocinnamic acid and β-ethyl-2-chlorohydrocinnamic acid; and aromatic unsaturated carboxylic acids, such as 2-, 3- or 4-methylcinnamic acid, 2-, 3- or 4-ethylcinnamic acid, 2-, 3- or 4-propylcinnamic acid, 2-, 3- or 4-butylcinnamic acid, 2-, 3- or 4-hydroxycinnamic acid, 2-, 3- or 4-methoxycinnamic acid, 2-, 3- or 4-ethoxycinnamic acid, 2-, 3- or 4-propoxycinnamic acid, 2-, 3- or 4-chlorocinnamic acid, 2-, 3- or 4-fluorocinnamic acid, 2-, 3- or 4-bromocinnamic acid, 2-methyl-3-ethylcinnamic acid, 3,4-dimethylcinnamic acid, 2,3-dimethoxycinnamic acid, 3,4-dimethoxycinnamic acid, α-methyl-3,4-dimethoxycinnamic acid, β-methyl-3,4-dimethoxycinnamic acid, 3,4-diethoxycinnamic acid, 2,4,5-trimethoxycinnamic acid, 2,4-dichlorocinnamic acid, 3,4-methylenedioxycinnamic acid and 3,4-trimethylenecinnamic acid. In the process of this invention, reactive functional derivatives of such aromatic carboxylic acids are used as a starting material. Examples of such derivatives include carboxylic acid derivatives, such as acid halides, acid anhydrides, mixed acid anhydrides and esters and a reaction product of such carboxylic acid and carbodiimide. These reactive functional derivatives can easily be derived from the aromatic carboxylic acids of the general formula (II) according to a usual technique known in this art. For example, the acid chlorides can easily be obtained by refluxing for several hours the aromatic carboxylic acid with thionyl chloride in the absence of any solvent or in dry benzene. The esters can be obtained by heating a given aromatic carboxylic acid with an alcohol in the presence of an acid. The mixed acid halides can be obtained, for example, by reaction with a chloroformic ester.

Any of anthranilic acid, m-aminobenzoic acid and p-aminobenzoic acid can be used as the aminobenzoic acid of the general formula (III). Any of anthranilic esters, m-aminobenzoic esters and p-aminobenzoic esters can be used as an aminobenzoic ester of the general formula (IV).

The above-mentioned amidation can be carried out according to methods known per se. For example, when an acid halide is used as the reactive functional derivative, the acid halide can be reacted in an inert solvent with an aminobenzoic acid of the general formula (III) or a derivative thereof of the general formula (IV) in the presence of a basic substance. In this case, a tertiary organic base such as trimethylamine, triethylamine or pyridine or an inorganic base such as a caustic alkali, sodium carbonate or potassium carbonate is used as the basic substance. Adequate as the inert solvent are chloroform, methylene chloride, acetone, benzene, toluene, tetrahydrofuran, dioxane and dimethylformamide.

Instead of using such a basic substance, the reaction may be carried out by using a compound of the general formula (III) in an excess amount, e.g., more than 2 molar proportion to the compound of the general formula (II).

The process of this invention is carried out preferably by dissolving a compound of the general formula (III) in a mixture of dry chloroform and dry pyridine respectively in amounts of 5–40 times and 2–15 times as much as the amount of the compound of the general formula (II), adding a solution of a compound of the general formula (II) in dry chloroform to the mixture under cooling and agitation and then refluxing the whole for several hours.

The reaction product is concentrated under reduced pressure and the residue is poured into water. Hydrochloric acid is then added to the aqueous mixture to make it weakly acidic. The precipitated crystals are collected by filtration and then recrystallized from an adequate organic solvent to obtain the end product.

In case a compound of the general formula (II) is an aromatic carboxylic acid carrying a hydroxyl group on the benzene nucleus, such compound is preferably protected in the hydroxyl group with acetyl group or the like prior to the reaction with a compound of the general formula (III). This protective group can be removed in the usual manner.

The resulting compound (I) carrying a carboxyl group can be converted according to usual methods to a physiologically acceptable salt thereof. For example, an aqueous solution of caustic soda in an equimolar amount can be added to an alcoholic solution of a compound of the general formula (I) and the mixture is warmed for an adequate period of time whereby the compound can easily be converted into its sodium salt. As examples of such physiologically acceptable salts there can be mentioned, in addition to the sodium salt, alkali metal salts, such as the potassium salt and lithium salt, alkali earth metal salts, such as the magnesium salt and calcium salts, salts with organic amines, such as piperidine, triethanolamine and diethylaminoethylamine, and the ammonium salt.

The aromatic carboxylic amide derivatives of this invention possess a special activity to the effects of an antigen-antibody reaction. Thus, they can be used widely as therapeutic medicaments for diseases caused by allergies.

This invention will be illustrated in more detail by way of examples wherein none of the melting points of the products have been corrected.

EXAMPLE 1

In a mixture of 20 ml of dry chloroform and 10 ml of dry pyridine were dissolved 2.6 g of 4-aminobenzoic acid. To this mixture were added dropwise under cooling 20 ml of dry chloroform containing 3.2 g of 4-acetoxycinnamoyl chloride. The mixture was heated under reflux for 2 hours and the reaction mixture was concentrated under reduced pressure. The residue was poured into water and hydrochloric acid was then added to make the liquid weakly acidic. The precipitated crystals were collected by filtration and recrystallized from alcohol to yield 2.9 g of 4-(4'-acetoxycinnamoylamino)-benzoic acid. M.P.=305°–307°C (with decomposition).

A mixture of 2.7 g of 4-(4'-acetoxycinnamoylamino)benzoic acid and 50 ml of a 10% aqueous solution of sodium hydroxide was warmed for one hour, cooled and then weakly acidified with hydrochloric acid. The precipitated crystals were collected by filtration and recrystallized from aqueous alcohol whereby 1.75 g of 4-(4'-hydroxycinnamoylamino)benzoic acid were obtained. M.P.=306°–307°C (with decomposition).

Elementary analysis as $C_{16}H_{13}O_4N$

|  | C | H | N |
|---|---|---|---|
| Calc. | 67.84% | 4.63% | 4.95% |
| Found | 67.69 | 4.56 | 4.72 |

IR-absorption spectra (KBr)
$\nu CO$: 1690, 1670 $cm^{-1}$
NMR spectra ($d_6$ - DMSO)
δ6.75, 7.58 (q, 2H J = 17 Hz, olefinic hydrogen)
6.90, 7.52 (q, 4H J = 8 Hz, hydroxy group-substituted aromatic ring hydrogen)
7.87, 7.96 (q, 4H J = 9 Hz, amino group-substituted aromatic ring hydrogen)
9.7 – 10.3 (broad, 1 H, amido hydrogen)
10.4 (s, 1 H, carboxylic acid hydrogen)
3.5 – 4.5 (broad, 1H, phenolic hydroxyl group hydrogen)
Mass spectra $M^+$ 283, m/e 238, 147, 119.

In 100 ml of warmed ethanol were dissolved 1.42 g of 4-(4'-hydroxy cinnamoylamino)benzoic acid. To this solution was added a solution of 0.21 g of sodium hydroxide in 3 ml of water and the mixture was warmed for 30 minutes, cooled and then filtered to collect crystals precipitated. 1.20 Grams of sodium salt of 4-(4'hydroxycinnamoylamino)benzoic acid were thus obtained.

The following compounds can be prepared in a similar manner:

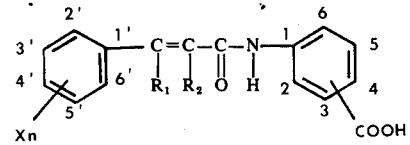

| Comp No | n | X | $R_1$ | $R_2$ | Pos. COOH | M.P. (°C) | Recrys. Solvent |
|---|---|---|---|---|---|---|---|
| 1 | 1 | 4'-OH | H | H | 2 | 220.5–221.5 | Aq.Alc. |
| 2 | 1 | 4'-OH | H | H | 4 | 306–307 (w/decomp.) | " |
| 3 | 1 | 2'-OH | H | H | 2 | 230–231 | " |
| 4 | 1 | 2'-OH | H | H | 3 | 267–268 | " |
| 5 | 2 | 2'-OH 3'-OMe | H | H | 2 | 206–208 | " |
| 6 | 2 | 2'-OH 3'-OMe | H | H | 4 | 307–307.5 (w/decomp.) | " |
| 7 | 2 | 4'-OH 3'-OMe | H | H | 2 | 230–232 | Alcohol |
| 8 | 2 | 4'-OH 3'-OMe | H | H | 3 | 238–239.5 | Aq.Alc. |
| 9 | 2 | 3'-OH 4'-OH | H | H | 2 | 204–206 (w/decomp.) | " |
| 10 | 3 | 2'-Br 4'-OH 5'-OMe | H | H | 2 | 249–250 | " |
| 11 | 2 | 4'-OH 3'-OMe | H | H | 4 | 250–251 | " |

EXAMPLE 2

In a similar manner except that 3-methoxy-4-acetoxyhydrocinnamoyl chloride was used in place of the 4-acetoxycinnamoyl chloride used in Example 1 for reaction with 3-aminobenzoic acid and the reaction product was hydrolyzed, 3-(3'-methoxy-4'-hydroxyhydrocinnamoyl amino)benzoic acid was obtained. After recrystallization from an aqueous alcohol, this product had a melting point of 218'220°C.

EXAMPLE 3

4.3 Grams of 4-aminobenzoic acid were dissolved in a mixture of 100 ml of dry chloroform and 19 g of dry pyridine. To this mixture were added dropwise under cooling 100 ml of a dry chloroform solution containing 5.4 g of 3,4-dimethoxycinnamoyl chloride. The mixture was heated under reflux for 1.5 hours and the reaction mixture was then concentrated under reduced pressure. The residue was poured into water and hydrochloric acid was then added to make the liquid weakly acidic. The precipitated crystals were collected by filtration and recrystallized from an alcohol whereby 5.6 g of 4-(3′,4′-dimethoxycinnamoylamino)benzoic acid were obtained. M.P.= 267°–9°C.

Elementary analysis as $C_{18}H_{17}O_5N$

|  | C | H | N |
|---|---|---|---|
| Calc. | 66.05% | 5.24% | 4.28% |
| Found | 66.00 | 5.12 | 4.14 |

IR-absorption spectra (KBr)
$\nu$CO: 1690, 1665 cm$^{-1}$
$\nu$NH: 3320 cm$^{-1}$ NMR spectra ($d_6$ - DMSO)
$\delta$6.78, 7.62 (q, 2H, J = 16 Hz olefinic hydrogen)
7.0–7.3 (m, 3H, methoxy-substituted aromatic ring hydrogen)
7.85, 7.97 (q, 4H, J = 9 Hz, amino-substituted aromatic ring hydrogen)
10.4 (s, 1H, carboxylic acid hydrogen)
11.5–12.7 (broad, 1H, amido hydrogen)
3.81, 3.83 (s, s, 6H, methoxy hydrogen)
Mass spectra
M$^+$ 327
m/e 282, 191, 163.

1.5 Grams of 4-(3′,4′-dimethoxycinnamoylamino)-benzoic acid were dissolved in 150 ml of warmed ethanol and an aqueous alcoholic solution (ethanol 2: water 1) of an equimolar amount of sodium hydroxide was added whereby white crystals precipitated out. The crystals were collected by filtration and dried under reduced pressure to obtain 1.0 g of sodium 4-(3′,4′-dimethoxycinnamoylamino) benzoate.

In a similar manner, the following compounds can be prepared:

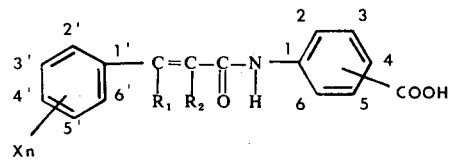

| Comp No | n | X | R$_1$ | R$_2$ | Pos. COOH | M.P. (°C) | Recrys. Solvent |
|---|---|---|---|---|---|---|---|
| 12 | 1 | 4′-OMe | H | H | 2 | 195–198 | Aq.Alc. |
| 13 | 1 | 4′-OMe | H | H | 4 | 292–294 | Alcohol |
| 14 | 1 | 3′-OMe | H | H | 2 | 183–185 | Aq.Alc. |
| 15 | 1 | 3′-OMe | H | H | 3 | 213–216 | " |
| 16 | 1 | 4′-OMe | CH$_3$ | H | 2 | 171–172 | " |
| 17 | 1 | 4′-OMe | CH$_3$ | H | 4 | 262–263 | Alcohol |
| 18 | 1 | 4′-OMe | H | CH$_3$ | 2 | 188–191 | Aq.Alc. |
| 19 | 1 | 4′-OMe | H | CH$_3$ | 3 | 244–246 | Alcohol |
| 20 | 1 | 4′-Cl | H | H | 2 | 195–203 | Aq.Alc. |
| 21 | 1 | 4′-Cl | H | H | 4 | 332–335 (w/decomp.) | " |
| 22 | 1 | 2′-Cl | H | H | 2 | 184.5–188.5 | " |
| 23 | 1 | 2′-Cl | H | H | 3 | 289–291 | " |
| 24 | 1 | 4′-Cl | CH$_3$ | H | 2 | 183–185 | " |
| 25 | 1 | 4′-Cl | CH$_3$ | H | 4 | 294–295 | Alcohol |
| 26 | 1 | 4′-Cl | H | CH$_3$ | 3 | 244–244.5 | " |
| 27 | 1 | 4′-Cl | H | CH$_3$ | 2 | 208.5–210.5 | Chlo. |
| 28 | 1 | 4′-F | H | H | 2 | 200–201.5 | Alcohol |
| 29 | 1 | 3′-F | H | H | 2 | 194–195.5 | " |
| 30 | 1 | 2′-F | H | H | 2 | 193–194.5 | " |
| 31 | 2 | 2′-OMe 3′-OMe | H | H | 2 | 198.5–200 | Aq.Alc. |
| 32 | 2 | 2′-OMe 3′-OMe | H | H | 4 | 261.263.5 | Alcohol |
| 33 | 2 | 3′-OMe 4′-OMe | H | H | 2 | 211–213 | Chlo. |
| 34 | 2 | 3′-OMe 4′-OMe | H | H | 3 | 225–226 | Alcohol |
| 35 | 2 | 3′-OMe 4′-OMe | H | H | 4 | 267–269 | " |
| 36 | 2 | 3′-OMe 4′-OMe | CH$_3$ | H | 2 | 173–175 | Aq.Alc. |
| 37 | 2 | 3′-OMe 4′-OMe | CH$_3$ | H | 3 | 163–164 | " |
| 38 | 2 | 3′-OMe 4′-OMe | CH$_3$ | H | 4 | 241–243 | Alcohol |
| 39 | 2 | 3′-OMe 4′-OMe | H | CH$_3$ | 2 | 169–172 | Aq.Alc. |
| 40 | 2 | 3′-OMe 4′-OMe | H | CH$_3$ | 3 | 203.5–204.5 | " |
| 41 | 2 | 3′-OMe 4′-OMe | H | CH$_3$ | 4 | 225.5–227.5 | Meth. |
| 42 | 1 | 4′-CH$_3$ | H | H | 2 | 210.5–213 | Aq.Alc. |
| 43 | 1 | 4′-CH$_3$ | H | H | 4 | 308–310 | " |
| 44 | 1 | 4′-Cl | C$_2$H$_5$ | H | 2 | 201–204 | " |
| 45 | 1 | 4′-OMe | H | C$_2$H$_5$ | 4 | 220–221.5 | " |

-continued

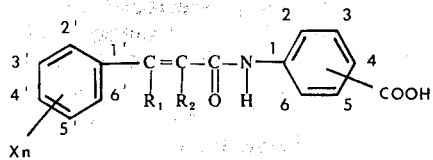

| Comp No | n | X | R₁ | R₂ | Pos. COOH | M.P. (°C) | Recrys. Solvent |
|---|---|---|---|---|---|---|---|
| 46 | 1 | 4'-Br | H | H | 2 | 222–225 | " |
| 47 | 1 | 4'-Br | H | H | 4 | >330 | Alcohol |
| 48 | 2 | 3'-OEt 4'-OEt | H | H | 2 | 185–187 | Aq.Alc. |
| 49 | 2 | 3'-OEt 4'-OEt | H | H | 4 | 253–256 | " |
| 50 | 2 | 4'-OEt 3'-OMe | H | H | 2 | 210.5–212.5 | " |
| 51 | 2 | 4'-OEt 3'-OMe | H | H | 3 | 219–222 | " |
| 52 | 3 | 2'-OMe 4'-OMe 5'-OMe | H | H | 2 | 206–208 | " |
| 53 | 2 | 3',4'-methylenedioxy | H | H | 2 | 209–210.5 | Alcohol |
| 54 | 1 | 3'-Cl | H | H | 2 | 194–196 | Aq.Ace. |
| 55 | 2 | 4'-O-n-Pro 3'-OMe | H | H | 2 | 172–177 | Chlo. |
| 56 | 2 | 4'-O-i-Pro 3'-OMe | H | H | 2 | 76–78 | " |
| 57 | 1 | 3-O-i-Pro | H | H | 2 | 121–124 | Benz/Pet. Ether |
| 58 | 1 | 4'-O-i-Pro | H | H | 2 | 140–142.5 | Benz./Pet. Ether |
| 59 | 1 | 4'-i-Pro | H | H | 2 | 153–156 | Iprop. Ether |
| 60 | 2 | 2'-OMe 3'-OMe | H | H | 3 | 238–240 | Alc./Ligroin |
| 61 | 2 | 2'-OMe 4'-OMe | H | H | 2 | 188–191 | Aq.Alc. |
| 62 | 2 | 2'-OMe 5'-OMe | H | H | 2 | 181–183 | " |

EXAMPLE 4

In a similar manner except that the cinnamoyl chloride used in Example 3 was replaced by the corresponding hydrocinnamoyl chloride, the following compounds could be prepared:

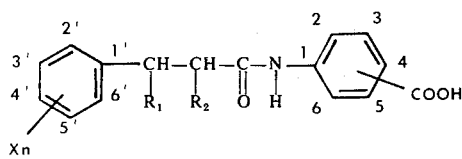

| Comp No | n | X | R₁ | R₂ | Pos. COOH | M.P. (°C) | Recrys. Solvent |
|---|---|---|---|---|---|---|---|
| 63 | 1 | 3'-OMe | H | H | 2 | 192–194.5 | Aq.Alc. |
| 64 | 2 | 3'-OMe 4'-OMe | H | H | 3 | 176–177 | Alc./Benz. |
| 65 | 1 | 4'-Cl | H | H | 4 | 278.5–280.5 | Aq.Alc. |
| 66 | 1 | 4'-OMe | H | CH₃ | 4 | 222–226 | " |
| 67 | 2 | 3'-OMe 4'-OMe | H | H | 2 | 136–137.5 | Benzene |

EXAMPLE 5

4 Grams of 3,4-dimethoxycinnamic acid was dissolved in 20 ml of dry pyridine. To this solution were added under cooling with ice and agitation 2 g of benzenesulfonyl chloride whereby a red orange precipitate was formed. The reaction mixture was stirred for about one hour and then 2 g of methyl anthranilate were added to the mixture under cooling with ice. The mixture was stirred for 2 hours at room temperature to complete the reaction. After completion of the reaction, the reaction mixture was concentrated and the residue was taken up in about 10 ml of chloroform. The solution was washed first with a 10% aqueous solution of caustic soda, then with a 10% aqueous solution of hydrochloric acid and finally with water and then distilled to remove chloroform whereby crystals of N-(3',-4'-dimethoxycinnamoyl)-anthranilic acid methyl ester were obtained.

This product was dissolved in 10 ml of chloroform. To this solution were added 10 ml of a 10% aqueous solution of caustic soda and the mixture was warmed at 50°C to effect hydrolysis of the ester group. After completion of the reaction, the organic phase was separated, washed with water and distilled to remove the solvent whereby 2.1 g (yield: 48%) of the end product, i.e., N-(3',4'-dimethoxycinnamoyl)-anthranilic acid, were obtained. This product had a melting point of 211°–213°C.

When the condensation reaction was carried out under similar conditions except that 1.9 g of anthranilic acid were used in place of methyl anthranilate used in this example, 2.0 g of N-(3',4'-dimethoxycinnamoyl)-anthranilic acid could directly be obtained.

EXAMPLE 6

2 Grams of 3,4-dimethoxycinnamic acid were dissolved in a mixture of 20 ml of dry dimethylformamide and 1.5 g of triethylamine. To this solution was added under ice cooling and agitation 1.1 g of ethyl chlorocarbonate and the mixture was then reacted for one hour. To this mixture were added 10 ml of dimethylformamide containing 1.5 g of 3-aminobenzoic acid and the mixture was stirred for 2 hours. After completion of the reaction, the reaction liquid was concentrated approximately to ½ volume and poured into an aqueous solution of hydrochloric acid. The precipitated crystals were separated by filtration, washed with water and recrystallized from an equivolume mixture of ethanol and water to obtain a yield of 50% 3-(3',4'-dimethoxycinnamoylamino)-benzoic acid having a melting point of 225°–226°C.

EXAMPLE 7

To a mixture of 20 ml of dry dioxane and 0.7 g of dry pyridine were added 2 g of 3,4-dimethoxycinnamic acid, 1.6 g of phosphorus oxychloride and 1.6 g of methyl anthranilate. The mixture was heated under reflux for 2 hours to effect reaction. After completion of the reaction, the reaction mixture was concentrated and the residue was dissolved with heating in ethanol and then cooled whereby crystals were precipitated. The crystals were separated by filtration and treated in a manner similar to that described in Example 5 to effect hydrolysis of the ester group. The product was recrystallized from chloroform to obtain 2 g of N-(3',-4'-dimethoxycinnamoyl)-anthranilic acid having a melting point of 211°–213°C.

EXAMPLE 8 — "Homologous Passive Cutaneous Anaphylaxis in Rats"

Wistar male rats weighing 120–150 g were used in this experiment. A reaginic antibody was obtained from rats immunized with egg albumin (EA) dissolved in the pertussis-diphtheria-tetanus vaccine. Normal rats were sensitized passively with dilution of the antibody by means of intradermal injection. After 48 hours of the sensitization, the mixture of antigen (EA) and evans blue was injected intravenously. The animals were killed by a blow on the head 30 minutes after the injection, and then the blue spot resulted from the antigen-antibody reaction was measured photometrically.

A given test compound dissolved in 1% NaHCO$_3$ solution was administered in a dose of 200 mg/kg orally 2 hours prior to the injection of antigen, while only the vehicle solution was administered to the control group. Chlorphenesin used as a positive control is generally well known as an inhibitor of mast cell disruption resulting from the allergic response.

The efficacy of the test compounds to inhibit the homologous passive cutaneous anaphlaxis was compared with the value (%) calculated using the following formula:

$$\frac{A - B}{A} \times 100$$

wherein A stands for the amount of leaked dye in control group and B for the amount of leaked dye in the group administered with a given test compound.

It seems likely that the homologous passive cutaneous anaphylaxis in rats is useful to determine whether a test compound inhibits an allergic response or not.

The results of the tests were as shown below.

| Test No. | Compound | Inhibition (%) |
|---|---|---|
| 1 | Control | 0 |
| 2 | Chlorphenesin | 36.7 |
| 3 | N-cinnamoyl-anthranilic acid | 16.7 |
| 4 | 3-(cinnamoylamino)-benzoic acid | 10.0 |
| 5 | 4-(cinnamoylamino)-benzoic acid | 7.0 |
| 6 | N-(4'-hydroxycinnamoyl)-anthranilic acid | 36.7 |
| 7 | 3-(3'-methoxycinnamoylamino-benzoic acid | 45.0 |
| 8 | N-(2'-chlorocinnamoyl)-anthranilic acid | 60.2 |
| 9 | N-(4'-chlorocinnamoyl)-anthranilic acid | 69.4 |
| 10 | 4-(4'-bromocinnamoylamino)-benzoic acid | 32.3 |
| 11 | N-(3'-fluorocinnamoyl)-anthranilic acid | 47.5 |
| 12 | N-(4'-methylcinnamoyl)-anthranilic acid | 54.0 |
| 13 | 4-(2'-hydroxy-3'-methoxycinnamoyl-amino)-benzoic acid | 33.5 |
| 14 | N-(2',3'-dimethoxycinnamoyl)-anthranilic acid | 56.8 |
| 15 | 3-(2',3'-dimethoxycinnamoyl-amino)-benzoic acid | 41.1 |
| 16 | N-3'-methoxy-4'-n-propoxycinnamoyl)-anthranilic acid | 52.2 |
| 17 | N-(3'-methoxy-4'-isopropoxycinnamoyl)-anthranilic acid | 47.1 |
| 18 | N-(3',4'-dimethoxycinnamoyl) anthranilic acid | 46.1 |
| 19 | N-(2',4',5'-trimethoxycinnamoyl)-anthranilic acid | 56.8 |
| 20 | N-(3',4'-dimethoxylhydrocinnamoyl)-anthranilic acid | 55.4 |
| 21 | N-(3',4'-dimethoxy-β-methylcinnamoyl)-anthranilic acid | 66.2 |
| 22 | N-[3'-methoxy-4'-(2,3-dihydroxypropoxy)-cinnamoyl]-anthranilic acid | 9.0 |
| 23 | N-(3'-methoxy-4'-carboxylmethoxycinnamoyl)-anthranilic acid | 0 |

The above results obviously show that in pharmacological activity, the new aromatic carboxylic amide derivatives of this invention are almost equal to or higher than Chlorphenesin. The nucleus-substituted cinnamoylaminobenzoic acid derivatives are generally stronger in the activity than the nucleus-unsubstituted cinnamoylaminobenzoic acid derivatives. However, the cinnamoylaminobenzoic acid derivatives nuclearly substituted by a hydrophilic group exhibit substantially no activity.

EXAMPLE 9 — "Effect on the Disruption of the Sensitized Mast Cells"

Mesenteric mast cells isolated from normal rats were sensitized passively by means of incubation with rat reaginic antibody at 37°C. After termination of the incubation, the specific antigen (DNP-Ascaris) was added to the incubation medium, then these mast cells in mesentery were fixed with formalin and stained with 0.1% toluidine blue (in acetic acid buffer; pH;4.6). The number of mast cells disrupted as a consequence of the antigen-antibody reaction were counted under a microscope. The number of the mast cells disrupted were also counted without the addition of the specific antigen.

A given test compound dissolved in 1% $NaHCO_3$ solution was added to the incubation medium at a concentration of $10^{-5}$ g/ml, 5 minutes prior to the treatment of antigen, while only the vehicle was added to the control group. Disodium cromoglycate used as positive control is generally well known as an inhibitor of mast cell disruption resulted in allergic response.

The efficacy of the test compounds to inhibit the mast cell disruption was compared with the value (%) calculated using the following formula:

$$\frac{(P-Q)-(R-Q)}{(P-Q)} \times 100$$

wherein P stands for the percentage of disrupted mast cells in the control group, Q for the percentage of mast cells disrupted spontaneously and R for the percentage of disrupted mast cells in the group treated with a given test compound.

It seems likely that this method is useful to determine whether a given test compound inhibits the disruption of mast cells and the subsequent release of chemical mediators from mast cells or not.

The results of the tests were as tabulated below.

| Test No. | Compound | Inhibition (%) |
|---|---|---|
| 1 | Control | 0 |
| 2 | Disodium cromoglycate | 16 |
| 3 | N-(3',4'-dimethoxycinnamoyl)-anthranilic acid | 33 |
| 4 | N-(3',4'-dimethoxy-β-methyl-cinnamoyl)-anthranilic acid | 45 |
| 5 | 3-(4'-methoxycinnamoylamino)-benzoic acid | 18 |
| 6 | N-(3'-methoxy-4'-n-propoxycinnamoyl)-anthranilic acid | 37 |

The above results obviously show that in pharmacological activity the novel aromatic carboxylic amide derivatives of this invention are almost equal to or higher than disodium cromoglycate.

EXAMPLE 10 — "Experimental Asthma in Rats"

Twenty normal male rats weighing 120–150 g were divided into four groups each consisting of five rats. 5 Milliliters of a 1% aqueous solution of $NaHCO_3$ containing 2-(3',4'-dimethoxycinnamolyamino)-benzoic acid (Compound 33 above) in a dose of 0 mg/kg, 5 mg/kg, 10 mg/kg or 20 mg/kg were orally administered to rats in each group respectively. After the lapse of two hours of the administration, all of the rats were sensitized passively by means of the intravenous injection of rat reaginic antibody. After a lapse of 24 hours of sensitization, both the trachea and the common carotide artery were canulated. The rate and volume of respiration and systemic blood pressure were recorded simultaneously on the polygraph. The results of these tests are shown in the annexed drawing. The asthmatic symptoms resulting from the injection of the specific antigen (DNP-Ascaris) were observed.

As is evident from the drawing, decrease in the rate of respiration was observed in the control after a lapse of three minutes from the injection of antigen. On the other hand, Compound No. 33 showed inhibition at a dose of 5 mg/kg or more. Concerning the decrease in the volume of respiration, this compound showed inhibition in a dose of 10 mg/kg or more. This compound showed no inhibiting effect on depression of blood pressure just after the challenge but showed an inhibiting effect on the subsequent depression.

EXAMPLE 10 — "Acute Toxicity"

The median lethal dose ($LD_{50}$) of the new aromatic carboxylic acid amide derivatives of this invention were determined in ddstrain male and female mice (6 weeks old) by oral administration and in Wistar strain male and female rats (7 weeks old) by oral and intraperitoneal administration. Each animal selected for the experiment was maintained in an airconditioned room at a temperature of 22°±1°C and a relative humidity of 55±5% during the full course of the experiment. All animals were fed compressed pellets (CE-2 type produced by Japan CLEA Co.) and water was available ad libitum by bottle. Five groups of ten animals for each administrative route were used.

Since these compounds were insoluble in water, they were suspended in a 0.5% aqueous solution of carboxymethylcellulose at each dosage level. The administrative volume of each agent to 10 g body weight mouse was 0.2 ml for oral administration, while that to 100 g body weight of rat was 0.5 ml for intraperitoneal and oral administrations.

The $LD_{50}$ values were calculated from the mortality on the eighth day by the Litchfield-Wilcoxon's method. The results of the tests were as tabulated below.

N-(3',4'-dimethoxycinnamoyl)-anthranilic acid
    Rats    1850 mg/kg    (o.)
              2030 mg/kg    (o.)
              385 mg/kg    (i.p.)
              338 mg/kg    (i.p.)
    Mice    705 mg/kg    (o.)
              500 mg/kg    (o.)
N-(2'-chlorocinnamoyl)-anthranilic acid
    Mice    343 mg/kg    (o.)
N-(4'-chlorocinnamoyl)-anthranilic acid
    Mice    551 mg/kg    (o.)
N-(3'-chlorocinnamoyl)-anthranilic acid
    Mice    700 mg/kg    (o.)
N-(2'-fluorocinnamoyl)-anthranilic acid
    Mice    321 mg/kg    (o.)
N-(3'-fluorocinnamoyl)-anthranilic acid
    Mice    551 mg/kg    (o.)
N-(4'-fluorocinnamoyl)-anthranilic acid
    Mice    481 mg/kg    (o.)

As demonstrated in Examples 8, 9, 10 and 11, the new aromatic carboxylic amide derivatives and functional derivatives thereof of this invention serve to inhibit not only cutaneous anaphylaxie and release of chemical mediators from mast cells but also experimental asthmatic symptoms caused by an antigen-antibody reaction. These results obviously show that the derivatives of this invention are effective for the therapeutic treatment of allergic diseases including asthma, hay fever, articaria and atopic dermatitis.

What is claimed is:

1. A compound selected from the group consisting of an aromatic carboxylic amide derivative of the formula:

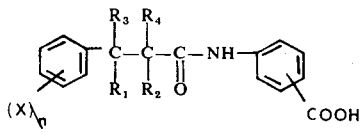

and therapeutically acceptable salts thereof, in which $R_1$ and $R_2$ are each a hydrogennatom or an alkyl group having 1–4 carbon atoms, $R_3$ and $R_4$ are each a hydrogen atom or together form another chemical bond, each X is a hydroxyl group, a halogen atom, an alkyl group having 1–4 carbon atoms and an alkoxy group having 1–4 carbon atoms, and $n$ is an integer of 1–3, provided that when two X's are said alkyl or alkoxy groups, the alkyl groups thereof may be connected together into an alkylene group.

2. A compound of claim 1 selected from the group consisting of a nucleus-substituted cinnamic amide of the general formula:

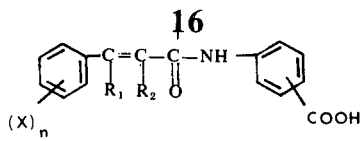

wherein $R_1$, $R_2$, X and $n$ have the same meanings as given above, and therapeutically acceptable salts thereof.

3. A compound of claim 2 wherein both $R_1$ and $R_2$ are hydrogen atoms.

4. A compound of claim 2 wherein at least one of $R_1$ and $R_2$ is an alkyl group having 1–4 carbon atoms.

5. A compound of claim 1 selected from the group consisting of a nucleus-substituted phenylpropionamide of the general formula:

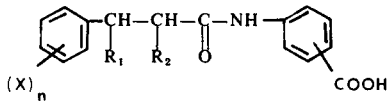

wherein $R_1$, $R_2$, X and $n$ have the same meanings as given above, and therapeutically acceptable salts thereof.

6. A compound of claim 5 wherein both $R_1$ and $R_2$ are hydrogen atoms.

7. A compound of claim 5 wherein at least one of $R_1$ and $R_2$ is an alkyl group having 1–4 carbon atoms.

* * * * *